United States Patent [19]

Schenk et al.

[11] Patent Number: 5,362,655
[45] Date of Patent: Nov. 8, 1994

[54] PROCESS FOR THE DETERMINATION OF A SPECIFICALLY BINDABLE SUBSTANCE

[75] Inventors: Roland Schenk, Weilheim; Dietmar Zdunek, Müchen, both of Germany

[73] Assignee: Boehringer Mannheim GmbH, Mannheim-Waldhof, Germany

[21] Appl. No.: 396,860

[22] Filed: Aug. 22, 1989

[30] Foreign Application Priority Data

Aug. 29, 1988 [DE] Germany .................. 3829245

[51] Int. Cl.$^5$ ............... G01N 33/555; G01N 33/566; A61K 35/14; A01N 1/02
[52] U.S. Cl. .................. 436/520; 436/500; 435/2; 435/261; 530/387.1
[58] Field of Search ........... 436/520, 500; 210/695; 435/2, 261; 530/387.1

[56] References Cited

U.S. PATENT DOCUMENTS

| | | | |
|---|---|---|---|
| 4,184,849 | 1/1980 | Cambiaso et al. | 436/500 |
| 4,690,899 | 9/1987 | Klose et al. | 436/45 |
| 4,829,011 | 5/1989 | Gibbons | 436/512 |
| 4,914,040 | 4/1991 | Lenz et al. | 436/175 |

FOREIGN PATENT DOCUMENTS

| | | |
|---|---|---|
| 0138297 | 4/1985 | European Pat. Off. |
| 0147848 | 10/1985 | European Pat. Off. |
| WO8805913 | 11/1988 | European Pat. Off. |
| 2013211 | 8/1979 | United Kingdom |

*Primary Examiner*—Margaret Parr
*Assistant Examiner*—Bradley L. Sisson
*Attorney, Agent, or Firm*—Felfe & Lynch

[57] ABSTRACT

For the determination of a specifically bindable substance by incubation of the sample solution with at least two receptors $R_1$ and $R_2$, whereby $R_1$ and $R_2$ are capable of binding to each other and $R_1$ is capable of specific binding to the substance to be determined and measurement of the agglutination which occurs in the reaction, a conjugate of one partner of a specific binding pair P and a component K capable of specific binding to the substance to be determined is used as the receptor $R_1$ and a receptor which has at least two binding sites for P is used as $R_2$.

13 Claims, 4 Drawing Sheets

PROCESS FOR THE DETERMINATION OF A SPECIFICALLY BINDABLE SUBSTANCE

The invention concerns a process for the determination of a specifically bindable substance by incubation of the sample solution with at least two receptors $R_1$ and $R_2$, whereby $R_1$ and $R_2$ are capable of binding to each other and $R_1$ is capable of binding to the substance to be determined, and measurement of the agglutination which occurs in the reaction as well as a suitable reagent therefor.

Very many substances are present in body fluids and tissues which are capable of binding to a specific binding partner and which serve as parameters for certain diseases or the state of health of the human body. These include, inter alia haptens such as e.g. hormones, proteins such as tumour markers, protein hormones and viral proteins, as well as antibodies. The determination of medicinal drugs in the blood is also often necessary to monitor drug therapy. Since these substances are often only present in very small amounts, procedures based on immunoassays are used for their detection. There are many variants of these. The different immunological methods of determination can be divided into homogeneous and heterogeneous procedures. A solid phase reaction is always part of a heterogeneous procedure in order to separate the bound from the unbound portion of the labelled component. In this type of procedure the label can be easily determined. A disadvantage is, however, the long duration of the heterogeneous reaction.

In the homogeneous procedure the bound label is not separated from the unbound label so that differentiation of bound and unbound label must be carried out by other methods.

There are different possibilities for this. For example, conjugated enzymes can be used as the label which only attain their enzymatic activity when they are bound to the hapten or antigen to be determined or when they are activated by the substance to be determined. A further possibility is to use a fluorescent substance as label whose fluorescence is either displaced into a different wavelength range or its polarization is changed by binding to the substance to be determined. A particular disadvantage of these new assays is that the sample often contains components which interfere with the test and this necessitates a pretreatment of the sample in order to eliminate these substances. In addition, time-consuming optimization is necessary for each parameter. For example, enzymes have to be modified depending on the parameter.

A procedure is known from EP-OS 79 962 in which the solution containing the hapten to be determined is brought into contact with latex particles coated with hapten or with albumin coated with hapten. An agglutination reaction takes place by addition of antibodies capable of binding to the hapten. Since the hapten bound to the latex particles or to the albumin competes with the hapten in the sample, the degree to which the agglutination reaction takes place is inversely proportional to the amount of hapten in the sample. The disadvantage of this procedure is that special particles have to be provided for each substance to be determined and each parameter has to be individually optimized.

A further procedure for the determination of protein which is based on the evaluation of an agglutination reaction is known from DE-OS 27 49 956. In this procedure antibodies against the substance to be determined are bound directly to particles which can be agglutinated. The reactivity of the antibodies can, however, be influenced by this binding. In addition, such a method of determination is susceptible to interferences by rheumatoid factors.

A disadvantage of all known competitive homogeneous agglutination immunoassays is that very time-consuming, parameter-specific optimization of the raw materials is necessary. In all these tests there are mutually opposing requirements for optimal differentiation and optimal sensitivity, since on the one hand the concentration of reagent in the form of particles should be limited in order to facilitate the competitive reaction with the sample and on the other hand the reagent in the form of particles should be in a high concentration and highly labelled in order to achieve a sufficient change in signal per unit time. Matching these requirements leads to limited sensitivity and susceptibility to interferences which can often only be eliminated by specific sample pretreatment.

The object of the present invention is therefore to provide a homogeneous method of determination which enables the detection of substances with high sensitivity and accuracy and which does not have the disadvantages described above.

This object is achieved by a process for the determination of a specifically bindable substance by incubation of the sample solution with at least two receptors $R_1$ and $R_2$, whereby $R_1$ and $R_2$ are capable of binding to each other and $R_1$ is capable of specific binding to the substance to be determined and measurement of the agglutination which occurs in the reaction, wherein a conjugate of one partner of a specific binding pair P and a component K capable of specific binding to the substance to be determined is used as the receptor $R_1$ and a receptor which has at least two binding sites for P is used as $R_2$.

The process according to the present invention is suitable for the determination of practically all substances in body fluids or tissue extracts which need to be detected and which are capable of specific binding, whereby substances at low concentrations can be detected as well as substances at high concentrations. The sensitivity and accuracy of this process is improved compared to the processes known up to now. The invention offers the possibility of carrying out rapid and reliable determinations with simple reagents.

The process is suitable for the determination of both monovalent specifically bindable substances as well as of bi- or polyvalent specifically bindable substances. A substance denoted as monovalent has only one binding site for a specifically bindable partner. Examples of this are haptens e.g. drugs. A substance is denoted as di- or polyvalent when it has two or more binding sites for a specifically bindable partner, such as protein hormones like HCG or TSH, antigens and proteins, tumour markers like CEA, vital proteins and antibodies.

In the description of the present invention an epitope is understood as a binding site which can participate in specific binding with another substance. Examples of epitopes are antigen determinants on antigens and haptens as well as specific binding sites on proteins.

For the determination of the substance to be detected, the sample solution is incubated with at least two receptors $R_1$ and $R_2$. The receptors $R_1$ and $R_2$ are capable of binding to each other and $R_1$ is, in addition, capable of specific binding to the substance to be determined. Various reaction principles can be carried out with the process according to the present invention. Each of FIG. 1a and FIG. 1b show a variant which is suitable for the detection of a bi- or polyvalent substance.

In the form of the procedure shown in FIG. 1a receptor $R_1$ which is a conjugate of one partner of a pair P which can specifically bind to one another and a component K which is capable of specific binding to the substance to be determined is added to a sample solution. Receptor $R_1$ then binds to the substance to be determined via component K which is an antibody in the diagram shown. In this process complexes form, whereby on each antibody two receptors $R_1$ are bound via K.

Receptor $R_2$, which has at least two and preferably a multitude of binding sites for P, is added at the same time as receptor $R_1$ or after a certain period of time. As a result receptor $R_1$ is bound to $R_2$ via P. Since each antibody has two receptors $R_1$ and thus two partners P capable of binding to $R_2$, cross-linkage or agglutination occurs which in turn causes a photometrically detectable turbidity or change in turbidity. The more antibody to be determined is contained in the solution the greater is the cross-linkage and the greater is the increase in turbidity. The extent of the agglutination is thus a direct measure of the substance to be determined. The evaluation of this is carried out using a calibration curve.

The variant of the procedure shown in FIG. 1b serves to detect polyvalent substances such as proteins which have a multitude of specific binding sites. The principle is the same as that shown in FIG. 1a. The substance to be determined in this case, however, can bind more than two receptors $R_1$, so that after addition of receptor $R_2$ not only linear cross-linkage but even three dimensional cross-linkage can occur. The extent of the agglutination is again a direct measure of the substance to be determined whereby a calibration curve is again used for the evaluation.

The process according to the present invention is equally suitable for carrying out so called uptake-tests. For this at least another receptor $R_3$ and if desired receptor $R_4$ are used. Two variants are shown in FIG. 2a and FIG. 2b. The preferred form of the procedure is shown in FIG. 2a. Here a process is specified for the determination of thyroxine binding capacity i.e. the amount of free binding sites which are made available by TBG (thyroxine binding globulin). For this type of assay a receptor $R_1$, which is a conjugate of thyroxine and biotin, and receptor $R_3$, which is an anti-$T_4$ antibody are added to the sample solution. In this process TBG in the sample solution which still has free binding sites for thyroxine competes with receptor $R_3$ for binding to thyroxine which is contained in receptor $R_1$. Either art the same time that $R_1$ and $R_3$ are added or after incubation of the sample with these, the receptor $R_2$ is added. $R_2$, in this case, is streptavidin. All complexes which form from TBG or receptor $R_3$ with receptor $R_1$ can bind to streptavidin. Cross-linkage can however only take place via complexes on which two receptors $R_1$ are bound to receptor $R_3$. The more TBG with free binding sites is present in the sample solution the more receptor $R_1$ binds to TBG and the smaller is the extent of the cross-linkage or agglutination and of the increase in turbidity. The increase in turbidity is thus an indirect measure of the content of free binding sites for thyroxine. A calibration curve can be used for the evaluation.

A variant of the uptake-test is shown in FIG. 2b. Here, in addition to the three receptors used in Example 2a, a further receptor $R_4$ is used which is thyroxine. After addition of receptors $R_1$, $R_3$ and $R_4$, TBG competes with free binding sites and with receptor $R_3$ for binding to receptors $R_1$ and $R_4$. Only those complexes in which receptor $R_1$ is bound can bind to $R_2$ after addition of receptor $R_2$. Only those complexes of receptor $R_3$ and two receptors $R_1$ can cross link, leading to an increase in turbidity following addition of receptor $R_2$. The more TBG with free binding sites present in the sample solution the more receptor $R_1$ is bound to TBG. These complexes of TBG and receptor $R_1$ cannot cross-link and they therefore diminish the extent of the cross-linkage and consequently the increase in turbidity. The increase in turbidity is also in this case an indirect measure of TBG with free binding sites present in the sample solution.

There are therefore many variants for carrying out the process defined in the present invention. In each case at least two receptors are necessary. The substance to be determined can be any substance capable of specific binding and in particular, as defined above, it can be a bivalent or polyvalent antigen, antibody or protein.

As a first receptor $R_1$ a conjugate is used which consists of a partner of a specific binding pair P and a component K capable of specifically binding to the substance to be determined. Pairs which bind specifically to each other are well known. Suitable binding pairs (P-$R_2$) are in particular biotin-streptavidin or avidin; hapten-antibody; antigen-antibody; concanavalin-antibody; sugar-lectin; hapten-binding protein; i.e. thyroxine binding globulin and thyroxine-antibody or oligopeptide-antibody.

Biotin with streptavidin or avidin is especially preferred as the binding pair, so that it is particularly preferable that receptor $R_1$ contains biotin.

The component K of receptor $R_1$ is capable of binding to the substance to be determined. Component K is selected according to the substance to be determined. A multitude of receptors are suitable for this. For the determination of haptens, proteins, DNA or sugar it is especially preferred to use antibodies or other receptors, such as naturally occurring binding proteins like thyroxine binding globulin, against these substances or fragments thereof. It is especially preferable to use a Fab-fragment as component K. For the determination of antibodies the component K is preferably a hapten or a substance which has an epitope capable of binding to the antibody.

The preparation of the conjugates is carried out according to known methods (e.g. analogous to *Eur. J. Biochem.* 131 (1980) 333–338).

The second receptor $R_2$ necessary for the process according to the present invention has at least two binding sites for P. Preferably $R_2$ presents a multitude of partners of a specific binding pair which bind to P. Receptor $R_2$ mediates the agglutination of the complex which forms during the reaction. Since there are a multitude of these other partners of the specific binding pair present in the reaction system, a small amount of a substance which occurs naturally in the sample solution which is capable of binding to this partner does not lead to interferences. The receptor $R_2$ can be a substance which already by nature has several binding sites for P such as streptavidin or antibody. Receptor $R_2$ can be polyvalent and have a multitude of binding sites for P or it can be a polymer of the partners of the specific binding pair which are complementary to P such as polystreptavidin. In this connection, the individual partners are either bound directly to each other or linked together via bridges. Processes for the production of such polymers are known to the expert and do not have to be elucidated further.

In a further embodiment the receptor $R_2$ consists of a carrier material on to which a multitude of the specific binding partners which bind to P are themselves bound. Particles can be used as carrier materials whose sizes are usually from 50 to 1000 nm. Suitable materials are polystyrene, finely dispersed silicon dioxide, erythrocytes or cross-linked albumin. The coating of these particles with the specific binding partner is carried out by methods known to the expert. Processes are described for example in EP-PS 73 611 and U.S. Pat. No. 4 703 018.

The receptors $R_2$ coated or polymerized in this way can be universally used for the process according to the present invention and are therefore not parameter specific.

To carry out the process according to the present invention it is essential that the receptor $R_1$ only has one binding site for $R_2$ i.e. that each receptor $R_1$ can only react with one $R_2$. This is an essential requirement since otherwise $R_2$ could be cross-linked by the receptor $R_1$ alone and this would result in agglutination which is not attributable to the substance to be determined.

When the process according to the present invention is used to carry out uptake-tests a further receptor $R_3$ is used which has at least two epitopes of the substance to be determined and which is capable of binding to $R_1$. The epitopes of receptor $R_3$ thus correspond to the epitopes of the substance to be determined which cause the binding to component K of $R_1$. An antibody or a Fab$_2$-fragment with binding sites for the component K is preferably used as the receptor $R_3$. When carrying out the process receptor $R_3$ then competes with the sample for binding to $R_1$.

In a further variant of the process according to the present invention a receptor $R_4$ is used in addition to receptor $R_3$. In this variant receptor $R_4$ is the component K of the receptor $R_1$. When carrying out the process receptor $R_3$ and the sample then compete for binding to receptor $R_1$ and receptor $R_4$.

The process can be carried out in one or more steps. The evaluation is carried out by measurement of the extent of the agglutination. Procedures for this are known. Photometric measurement of turbidity, the measurement of scattered light by nephelometry, particle counting or photon-correlation-spectroscopy (PCS) are for example suitable.

Since each of the receptors and also the substance to be determined can only react specifically with its own particular reaction partner, it is possible to incubate all receptors and the sample together and to carry out the process in one step. This is particularly advantageous when carrying out the process in an automated analyzer.

All variants of the process are preferably carried out in a buffered solution. Buffer systems for these processes are known. Particularly suitable are GOOD-buffers and phosphate buffer.

According to the present invention a process is provided which is simple and fast to carry out and which provides a measurement reading that is dependent on the concentration of the substance to be determined. Since the system responsible for the immunological competition and the system which forms the signal are separated, the sensitivity of the detection is increased. In this way even substances in low concentrations can be quantitatively, rapidly and reliably determined with simple reagents.

A further embodiment of the present invention is a reagent for the determination of a specifically bindable substance, wherein it contains receptor $R_1$ which is a conjugate of one partner of a specific binding pair and a component K capable of specific binding to the substance to be determined, and receptor $R_2$ which has at least two binding sites for P.

The reagent according to the present invention can contain the individual receptors $R_1$ and $R_2$ and if desired $R_3$ and $R_4$ in a premixed form or physically separated from each other.

This reagent is suitable for the determination of very many parameters in body fluids and tissue extracts.

In a preferred embodiment the reagent contains in addition buffer substances. It is particularly preferred that it contains phosphate buffer or GOOD-buffer.

The invention is elucidated by the Figures and the Examples.

In all variants shown streptavidin is used as receptor $R_2$, which has four binding sites for P. In each case a conjugate of a receptor capable of specifically binding to the substance to be determined and biotin is used as receptor $R_1$.

Figure 1A:
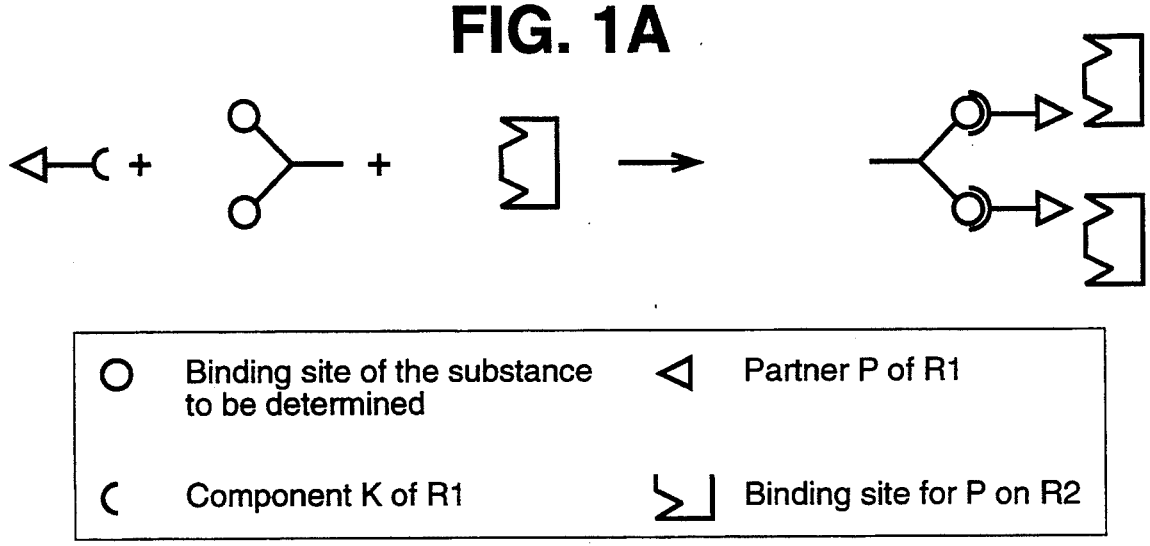
FIGS. 1a and 1b show a diagram of two reaction principles of the process according to the present invention.
Figure 1B:
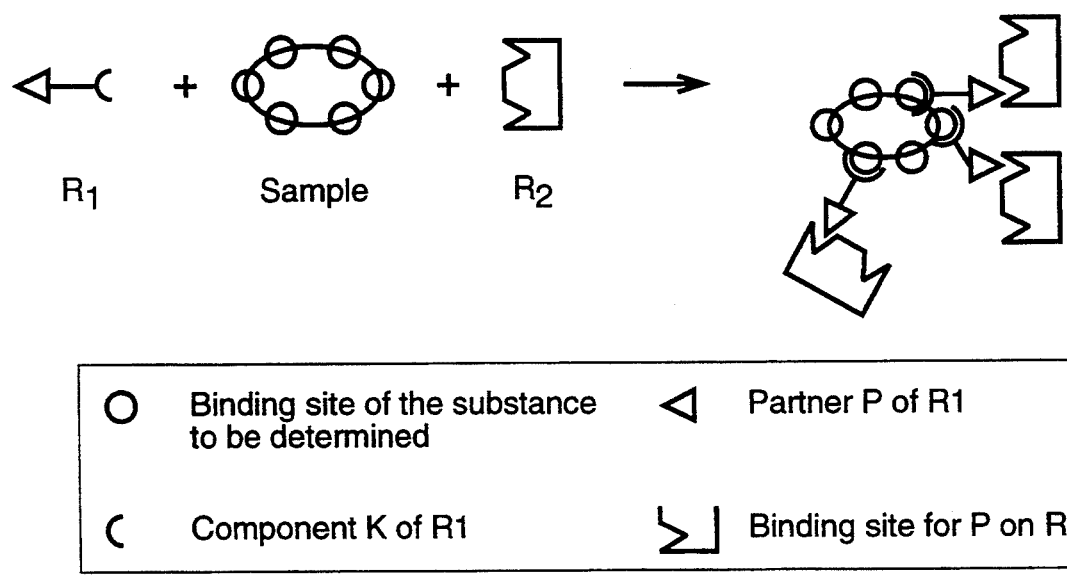

FIG. 1a shows a variant which is suitable for the detection of antibodies. For this receptor $R_1$ contains an epitope which is capable of binding to the antibody to be determined.

Variant 1b may be used to determine polyvalent substances e.g. proteins.

Figure 2A:
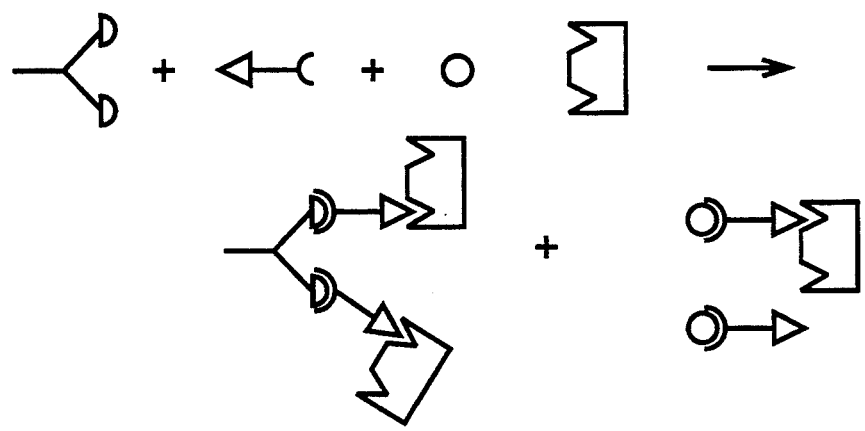
FIGS. 2a and 2b show a diagram of two reaction principles for uptake-tests.

FIG. 2a shows a variant for carrying out an uptake-test for thyroxine. In this case, in addition to the receptors $R_1$ and $R_2$ described above, a receptor $R_3$ is used which is an anti-$T_4$ antibody.

Figure 2B:
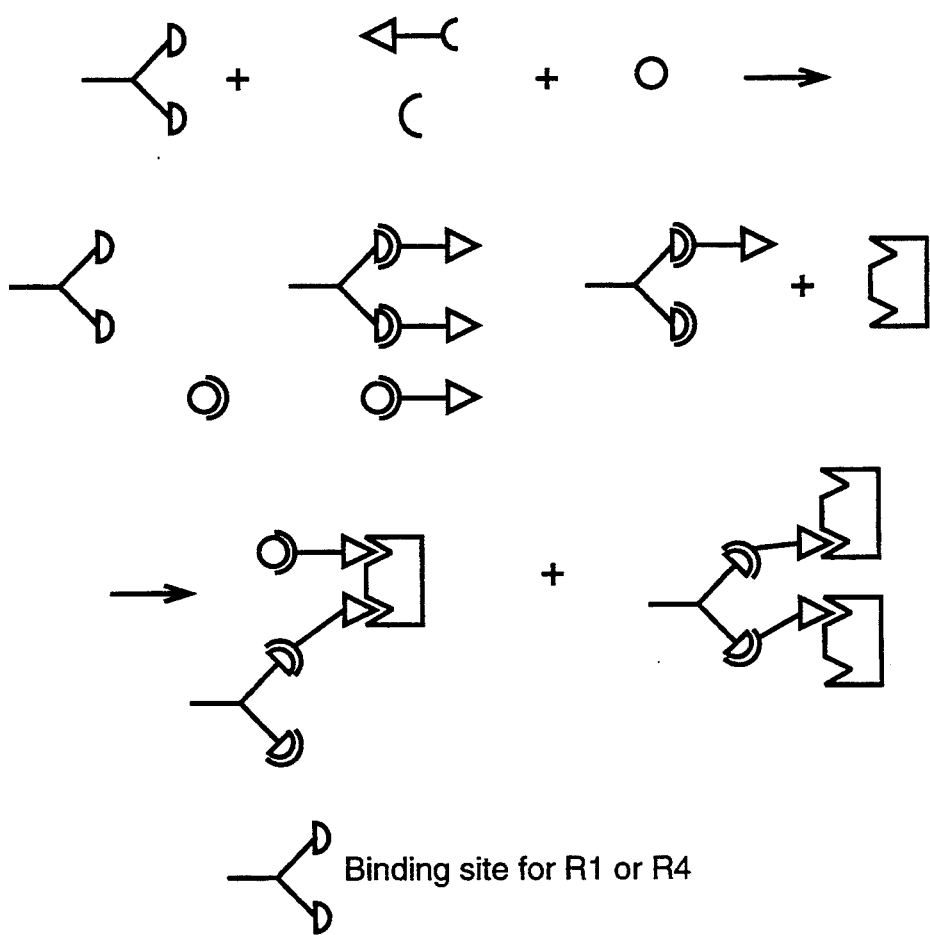

The variant shown in FIG. 2b is a further method for carrying out an uptake-test in which, in addition to the receptors $R_1$, $R_2$ and $R_3$, thyroxine is used as receptor $R_4$.

Figure 3:
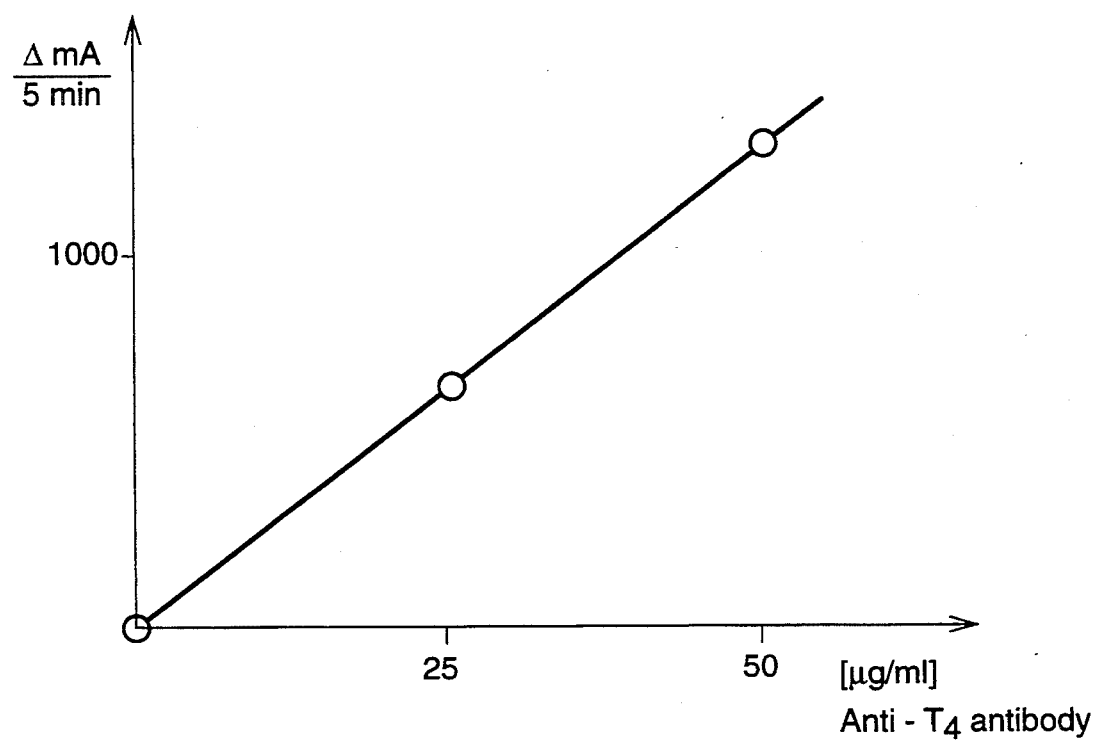

FIG. 3 shows a calibration curve for an anti-$T_4$-antibody test

Figure 4:
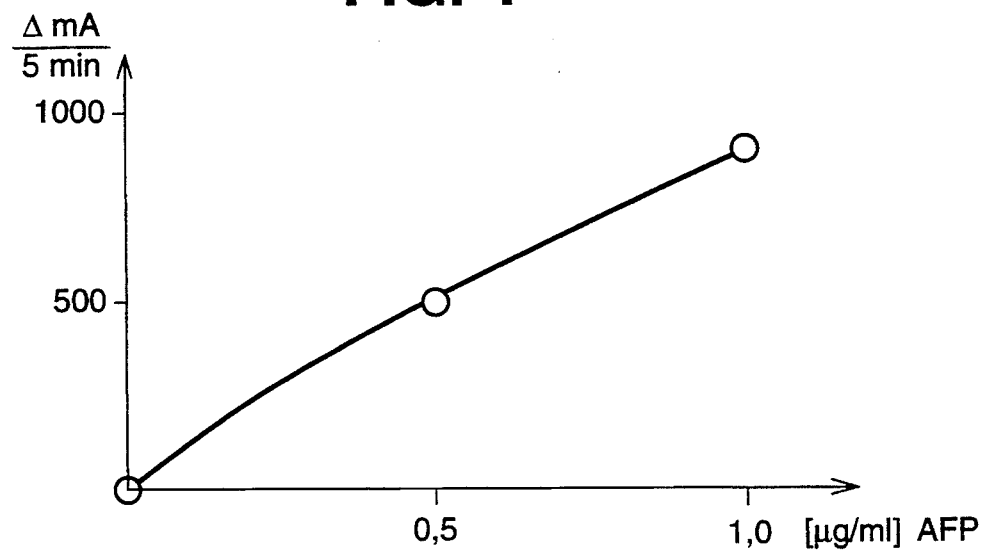

FIG. 4 shows a calibration curve for an AFP (alpha fetal protein) determination

Figure 5:
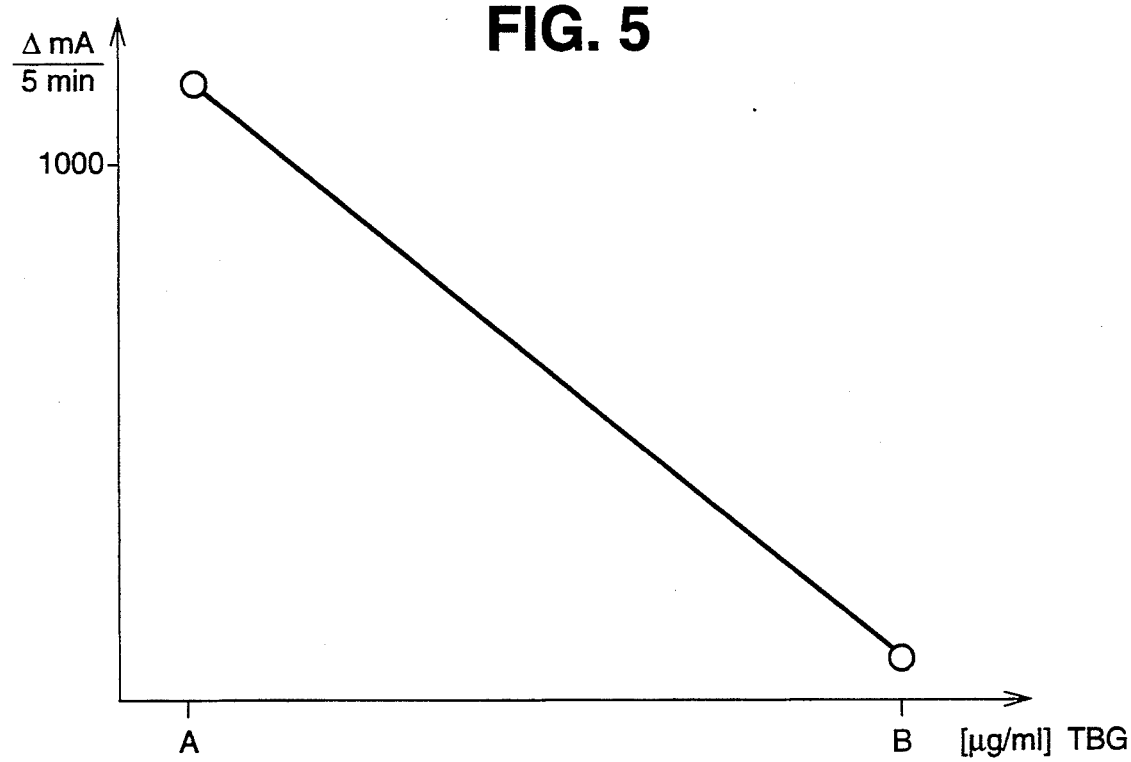

FIG. 5 shows a calibration curve for a T-uptake test (principle analogous to FIG. 2a)

Figure 6:
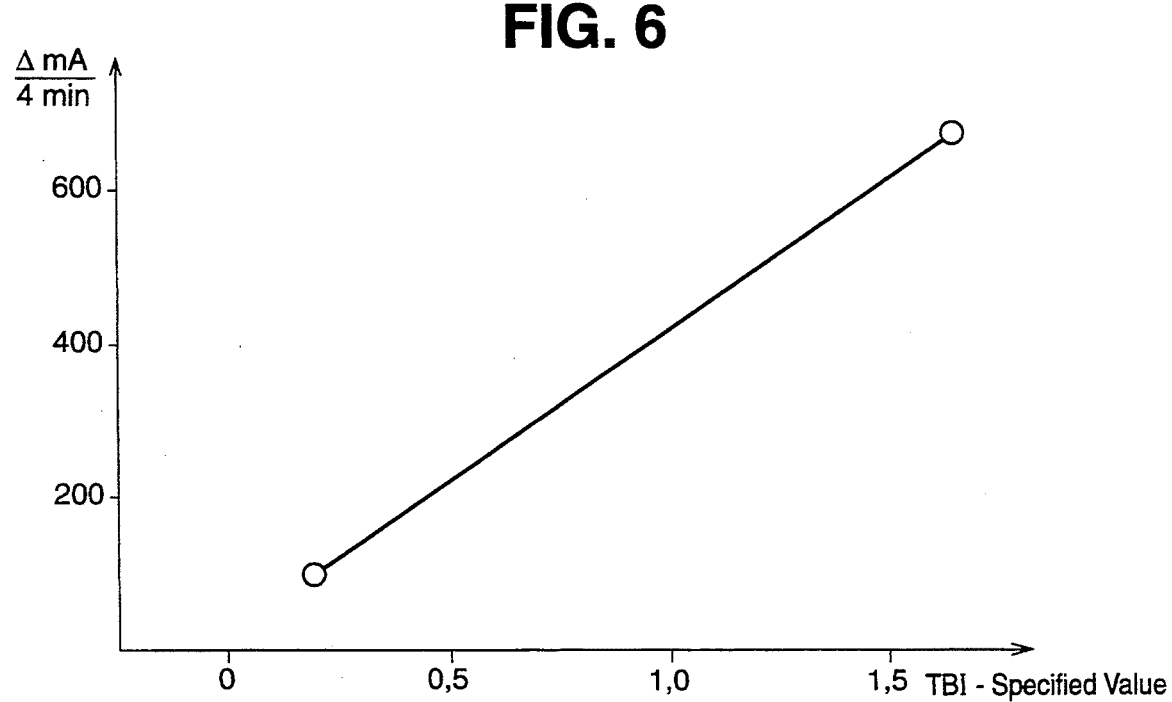

FIG. 6 shows a calibration curve for a T-uptake test by variation of the amount of $T_4$ (principle analogous to FIG. 2b)

EXAMPLE 1 a) Preparation of streptavidin-latex

Streptavidin at a concentration of 2 mg/ml in 15 mmol/l imidazole buffer, pH 7.5, 100 mmol/l NaCl is incubated together with chlormethylstyrene particles (latex, d = 70 nm, corresponding to USP 4 703 018) at a concentration of 2% by weight for 24 h at 55° C and stirred. After centrifugation of the reaction mixture for 60 minutes at 20000 r.p.m. the supernatant is decanted and the precipitate resuspended in 200 mmol/l glycine buffer, pH 7.5, containing 0.5% bovine serum albumin. A 1% by weight streptavidin-latex reagent is prepared by appropriate dilution.

b) Preparation of hapten-biotin conjugates

For this n-butyloxy-carbonyl-tetraiodothyronine (DE-A 28 05 961) is coupled via pentamethylene-diamine with biotin as described in Eur. J. Biochem. 131 (1980) 333–338. One obtains a $T_4$-biotin conjugate.

EXAMPLE 2

Determination of an antibody against $T_4$

Reagent 1

0.1 μmol/l $T_4$-biotin conjugate
0.1 mol/l sodium barbiturate buffer pH 8.5
2% by weight dextran

Reagent 2

10 mg/ml streptavidin-latex
200 mmol/l glycine buffer pH 7.5
0.1% by weight sodium azide
A polyclonal antibody against $T_4$ in physiological saline, containing in addition 0.1% non-specific sheep immunoglobulin (IgG), is used as sample.

Procedure for the determination

20 μl of sample and 960 μl of reagent 1 are incubated for 5 minutes at 37° C. Afterwards the agglutination reaction is started by addition of 20 μl of reagent 2 and the change in optical density per unit time is measured in a photometer at 405 nm. The result is shown in FIG. 3.

EXAMPLE 3

Determination of AFP (α-fetal protein)

a) Preparation of a conjugate of biotin and Fab-fragments of anti-AFP antibodies (anti-AFP-Fab-biotin)

Polyclonal antibodies against AFP are purified by immunosorption and coupled to biotin according to Analyt. Biochem. 161 (1987) 262–271 or Analyt. Biochem. 149 (1985) 529–536.

b) Test procedure

Reagent 1

5 μg/l anti-AFP-Fab-biotin
0.1 mol/l sodium barbiturate buffer pH 8.5

Reagent 2

10 mg/ml streptavidin-latex
0.2 mol/l glycine buffer pH 7.5
0.1% by weight sodium azide
AFP in human serum is used as sample 50 μl of sample and 900 μl of reagent 1 are incubated for 5 minutes at 37° C. Afterwards the agglutination reaction is started by addition of 20 μl of reagent 2 and the change in optical density per unit time is measured in a photometer at 405 nm. The result is shown in FIG. 4.

EXAMPLE 4

T-uptake test (reaction principle according to FIG. 2a)

The principle of the test is that an anti-$T_4$ antibody and a $T_4$-biotin conjugate compete for the TBG (thyroxine binding globulin) in the sample.

Procedure for the determination

Reagent 1

40 nmol/l $T_4$-biotin conjugate
0.1 mol/l sodium phosphate buffer pH 7.5
1% by weight dextran sulphate

Reagent 2

0.1 mg/ml polyclonal anti-$T_4$ antibody from sheep (IgG)
10 mg/ml streptavidin-latex
200 mmol/l glycine buffer pH 7.5
0.1% by weight sodium azide
A physiological saline solution (A) and 100 μg/ml TBG in physiological saline (B) are used as samples.

20 μl of sample and 960 μl of reagent 1 are incubated for 5 minutes at 37° C. Afterwards the agglutination reaction is started by the addition of 20 μl of reagent 2 and the change in optical density per unit time is measured in a photometer at 405 nm. The result is shown in FIG. 5

EXAMPLE 5

T-uptake test (reaction principle according to FIG. 2b)

The determination is carried out in the following manner: $T_4$ is added to the sample to saturate excess TBG. Afterwards the unbound $T_4$ is measured. By this means a calibration curve is obtained which is directly proportional to the thyroxine binding index (TBI).

Reagent 1

1 μg/ml $T_4$
0.1 mol/l sodium phosphate buffer pH 7.5

Reagent 2

0.1 mol/l sodium barbiturate buffer pH 8.5
2% by weight dextran sulphate
0.2 mg/ml streptavidin-latex
2 μg/ml polyclonal anti-$T_4$ antibody from sheep (IgG)

Reagent 3

2 μmol/l $T_4$-Biotin conjugate in ethanol/water (1:1)
Human serum is used as the sample which has defined specified values for the thyroxine binding index (TBI) (sample A:0.19 TBI, sample B:1.64 TBI)

Procedure for the determination

20 μl of sample and 20 μl of reagent 1 and 900 μl of reagent 2 are incubated for 5 minutes at 37° C. Afterwards the agglutination reaction is started by the addition of 20 μl of reagent 3 and the change in optical density per unit time is measured in a photometer at 405 nm. The result is shown in FIG. 6.

We claim:

1. Method of determining the presence of a specifically bindable substance in a sample solution, comprising: incubating a sample solution with at least two receptors $R_1$ and $R_2$, wherein $R_1$ and $R_2$ bind to each other, wherein $R_1$ has only one binding site for $R_2$, specifically binds to the substance to be determined and contains (i) P, a first member of a specific binding pair, and (ii) a component K which specifically binds to the substance t be determined, and $R_2$ comprises a plurality of second members of said specific binding pair, wherein each of said plurality of second members has at least two binding sites for P, under conditions favoring agglutination of $R_1$, and $R_2$, and said substance to be determined, and measuring said agglutination to determine the presence of said specifically bindable substance.

2. Method of claim 1, wherein said specifically bindable substance to be determined has at least two epitopes which bind to component K, which is a part of receptor $R_1$.

3. Method of claim 1, wherein said specific binding pair is selected from the group consisting of biotin-streptavidin, biotin-biotin specific antibody, antigen-antigen specific antibody, hapten-hapten binding protein and oligopeptide-oligopeptide specific antibody.

4. Method of claim 1, wherein $R_2$ comprises a particulate carrier ranging in size from 50 nm to 1000 nm having bound thereon said plurality of second members of said specific binding pair.

5. Method of claim 4, wherein said particulate carrier comprises a polystyrene sphere, silicon dioxide, or an erythrocyte.

6. Method of claim 1, wherein $R_2$ comprises a polymer of second members of said specific binding pair.

7. Method of claim 1 wherein K is an Fab fragment of an antibody.

8. Method of claim 1 further comprising incubating said sample with a third receptor $R_3$ having at least two epitopes of the substance to be determined wherein $R_3$ specifically binds to K.

9. Method of claim 8, wherein $R_3$ comprises an antibody or a $Fab_2$-fragment thereof.

10. Method of claim 8, further comprising incubating said sample with a fourth receptor $R_4$ which contains an additional molecule of component K.

11. Reagent for the determination of a specifically bindable substance comprising a first receptor $R_1$ consisting of a conjugate of (i) P, a first member of a specific binding pair and (ii) a component K, which specifically binds to the substance to be determined, and a second receptor $R_2$ which comprises a plurality of second members of said specific binding pair, wherein each of said plurality of second members has at least two binding sites for P wherein $R_1$ has only one binding site for $R_2$, and $R_1$ and $R_2$ are physically separated from each other in said reagent.

12. Reagent of claim 11, further comprising a third receptor $R_3$ which comprises at least two epitopes of the substance to be determined, each of which specifically binds to K.

13. Reagent of claim 12, further comprising a fourth receptor $R_4$ which contains an additional molecule of component K.

* * * * *